US00RE34990E

United States Patent [19]

Khanna et al.

[11] E Patent Number: Re. 34,990

[45] Reissued Date of Patent: Jul. 4, 1995

[54] ORAL THERAPEUTIC SYSTEM HAVING SYSTEMIC ACTION

[75] Inventors: Satish C. Khanna, Bottmingen; Theresa Ruttimann, Basel, both of Switzerland

[73] Assignee: Ciba-Geigy Corporation, Ardsley, N.Y.

[21] Appl. No.: 133,814

[22] Filed: Oct. 8, 1993

Related U.S. Patent Documents

Reissue of:

[64] Patent No.: 4,857,336
Issued: Aug. 15, 1989
Appl. No.: 79,055
Filed: Jul. 29, 1987

U.S. Applications:

[63] Continuation of Ser. No. 619,160, Nov. 28, 1990, abandoned.

[51] Int. Cl.[6] ..... A61K 9/24

[52] U.S. Cl. ..... 424/473; 424/469; 424/484; 424/485; 424/486; 424/488

[58] Field of Search ..... 424/484, 473, 485, 486, 424/488, 469

[56] References Cited

U.S. PATENT DOCUMENTS

| | | | |
|---|---|---|---|
| 3,845,770 | 11/1974 | Theeuwes et al. | 128/260 |
| 4,111,202 | 9/1978 | Theeuwes | 128/260 |
| 4,327,725 | 5/1982 | Cortese et al. | 128/260 |
| 4,409,212 | 10/1983 | Mondadori | 424/244 |
| 4,431,641 | 2/1984 | Mondadori | 424/244 |
| 4,553,973 | 11/1985 | Edgren | 424/427 X |
| 4,685,918 | 8/1987 | Amidon et al. | 604/892 |
| 4,716,031 | 12/1987 | Eckenhoff et al. | 424/457 X |

FOREIGN PATENT DOCUMENTS 2150830 7/1985 United Kingdom .

OTHER PUBLICATIONS

Theeuwes, J. Pharm. Sci., 64, (12) pp. 1987-1991 (1975).
Derwent Abstract of Acta Pharm. Fenn., 94 (2) p. 75 (1985).
H. Kala et al, Pharmazie 41, pp. 61-62 H. 1 (vol. 1) 1986.

*Primary Examiner*—Edward J. Webman
*Attorney, Agent, or Firm*—Irving M. Fishman; Karen G. Kaiser

[57] ABSTRACT

The invention relates to a therapeutic system for peroral administration and having systemic action, which system is in the form of a coated and/or laminated monocompartment system for administering carbamazepine. The therapeutic system comprises (a) a wall made of a material which is permeable to water and impermeable to the components of the drug-containing core, (b) a core containing finely particulate carbamazepine as drug and, as auxiliaries, a protective colloid that inhibits the crystal growth of carbamazepine in the presence of water, a swellable hydrophilic polymer and, optionally, a water-soluble compound for inducing osmosis and/or further pharmaceutically acceptable excipients, and (c) a passageway through the wall (a) for delivering the core components to the environmental body fluid. The therapeutic system can be used as an anticonvulsive for the treatment of convulsive states, especially epileptic states.

15 Claims, No Drawings

ORAL THERAPEUTIC SYSTEM HAVING SYSTEMIC ACTION

Matter enclosed in heavy brackets [ ] appears in the original patent but forms no part of this reissue specification; matter printed in italics indicates the additions made by reissue.

*This application is a continuation of application Ser. No. 07/619,160, filed Nov. 28, 1990, now abandoned which was a reissue of Ser. No. 07/079,055, filed Jul. 29, 1987, now U.S. Pat. No. 4,857,336, issued Aug. 15, 1989.*

The present invention relates to an oral therapeutic system for carbamazepine with a compartment for the drug formulation, and to a process for the preparation thereof as well as to the therapeutic use of said system as anticonvulsant.

Carbamazepine, 5H-dibenz[b,f]azepine-5-carboxamide (Tegretol®, Tegretal®, Ciba-Geigy) is used as anticonvulsant and analgesic. Commercial dosage forms are 200 mg tablets and 2% syrups.

Oral therapeutic systems for effecting a systemic action and their advantages over conventional dosage forms such as tablets and syrups are known. By means of such systems it is possible to achieve a prolonged release of active substance at a constant therapeutic level. In the OROS® system (oral osmotic system; Alza Corp.), which has been described by F. Theeuwes in J. Pharm. Sc., Vol. 64, 12 1987–1991 (1975), and which is in the form of a conventional tablet, aqueous body fluids enter the system continuously through the outer layer acting as semi-permeable membrane and dissolve the solid active substance core. Given sufficient water-solubility, the pressure that is built up causes the solution containing the drug to be released through an orifice having a diameter of c. 100–150 μm.

When the active substance present in the core is able to produce a sufficiently high osmotic pressure of its own, this dosage form effects the release of a sufficient amount of the drug and thus achieves the desired therapeutic effect. The prerequisite for achieving this effect is a sufficiently high concentration of water-soluble drug and a correspondingly low concentration of excipients in the core.

For this reason OROS® systems are unsuitable for sparingly soluble drugs. In particular, the osmotic pressure of a drug such as carbamazepine, which is administrable in high dosage, is too low. To solve this problem U.S. Pat. No. 4 111 202 postulates the use of two-compartment systems for sparingly soluble drugs ("push-pull" systems), which systems contain the drug or drug formulation in one compartment and water-soluble auxiliaries, e.g. salts or sugars for producing an osmotic pressure, in a second compartment underneath. The two compartments are separated from each other by a flexible partition and sealed externally by a rigid but water-permeable semi-permeable membrane. When water enters the compartment, the osmotic pressure thereby produced causes an increase in volume of the lower compartment. As the semi-permeable wall is rigid, the osmotic pressure acts solely on the expanding flexible partition and expels the contents of the drug compartment from the system.

The preparation of push-pull systems is technically complicated, as a flexible partition consisting of a material different from that of the semi-permeable membrane has to be incorporated into such a dosage form. In addition, for sparingly soluble high-dosage drugs like carbamazipine, which is administered in a dosage of e.g. more than 200 mg, it is only possible to prepare voluminous push-pull systems whose ingestion, especially after an epileptic attack, is problematical.

Push-pull systems for sparingly soluble drugs without a partition are disclosed in European patent application No. 52917. The osmotic driving member is present in the drug compartment. The compartment underneath consists of a swellable polymer such as polyvinylpyrrolidone. The osmotic pressure built up effects a increased absorption of fluid into the system, whereby the swelling is accelerated. The pressure exerted by swelling effects an expansion in volume only of that compartment which consists of swellable polymer and, as the semi-permeable membrane is rigid, expels the contents of the drug compartment through an orifice.

The dosage form disclosed in European patent application No. 52917 is to be understood as a two-layered tablet with coating. Compared with conventional coated tablets, the preparation of these tablets is complicated. Thus the compression must be carried out in two steps. In the usual compression of different granulates, stringent demands are made of the uniform particle size of the granulate components that are compressed together. Reference is made in this connection to the description of multi-layered tablets and the technical problems and requirements made of the granulates employed in "Hagers Handbuch der Pharmazeutischen Praxis", Springer Verlag 1971 (hereinafter referred to for short as "Hager"), Vol. VIIa, p. 710 bottom and p. 733 bottom to p. 725.

A further problem is that, when using anhydrous carbamazepine (amorphous or crystalline), dihydrates form on contact with water (q.v. J. Pharm. Soc. Jpn. No. 2, 184–190, 1984). The dihydrates are in the form of needles which may grow to a particle size of c. 500 μm in length. The known push-pull systems cannot function satisfactorily with such dihydrate crystals, as the expanded bulky crystals block the orifice of the therapeutic system. Therefore only milled carbamazepine crystals whose maximum size is governed by the diameter of the orifice of the system are suitable. Up to now it has only been possible to obtain mill carbamazepine dihydrate crystals of suitable size by means of the wet milling process. Because the grinding stock has to be dried, dry milling processes are problematical, for the anhydrous carbamazepine forms again at c. 37° C. The wet milling process itself also has disadvantages, as the suspension agent has to be removed in a separate step.

It is the object of the present invention to provide an oral therapeutic system for carbamazepine having only one drug compartment, the size of which corresponds to that of the known prior art oral osmotic monocompartment systems, and to prevent the crystal growth of carbamazepine by addition of a suitable auxiliary, so that the two cumbersome steps of preparing the hydrate form and wet milling are avoided.

This object is achieved by choice of a suitable protective colloid which inhibits the crystal growth of carbamazepine hydrate forms in oral osmotic systems, keeps the particle size of the hydrate crystals substantially constant, and effects a sufficient rate of release from the monocompartment system.

The invention relates to a therapeutic system having systemic action for peroral administration in the form of a coated and/or laminated monocompartment system for the administration of carbamazepine. The therapeutic system of the invention comprising (a) a wall made of a material which is permeable to water and impermeable to the compartments of the drug-containing core, (b) a core containing finely particulate carbamazepine as drug and, as auxiliaries, a protective colloid that inhibits the crystal growth of carbamazepine in the presence of water, a swellable hydrophilic polymer and, optionally, a water-soluble compound for inducing osmosis and/or further pharmaceutically acceptable excipients, and (c) a passageway through the wall (a) for delivering the core components to the environmental body fluid.

The invention further relates to a process for the preparation of said oral therapeutic system and to a method of inhibiting the crystal growth of carbamazepine hydrate forms in an oral therapeutic system, as well as to the use of said system as anticonvulsant and/or analgesic.

The definitions and terms employed throughout this specification have the following preferred meanings within the scope of the description of this invention.

The wall (a) made of material which is permeable to water and impermeable to the components of the active substance core may be understood as being a semi-permeable membrane which is permeable to the passage of water but substantially impermeable to the passage of components present in the core of the dosage form, e.g. drug, swellable polymer, osmotic agent and the like.

Suitable materials for forming the semi-permeable wall are e.g. the polymeric microporous materials described in the literature, e.g. in U.S. Pat. Nos. 3,916,899 and 3,977,404, and which are not metabolised in the gastrointestinal tract, i.e. which are excreted intact. For example, it is possible to use acylated cellulose derivatives (cellulose esters) which are substituted by one to three acetyl groups or by one or two acetyl groups and a further acyl radical other than acetyl, e.g. cellulose acetate, cellulose triacetate, agar acetate, amylose acetate, cellulose acetate ethyl carbamate, cellulose acetate phthalate, cellulose acetate methyl carbamate, cellulose acetate succinate, cellulose acetate dimethylaminoacetate, cellulose acetate ethyl carbonate, cellulose acetate chloroacetate, cellulose acetate ethyl oxalate, cellulose acetate methyl sulfonate, cellulose acetate butyl sulforate, cellulose acetate propionate, cellulose acetate diethylaminoacetate, cellulose acetate octate, cellulose acetate laurate, cellulose acetate p-toluenesulfonate, cellulose acetate butyrate and other cellulose acetate derivatives. Suitable semi-permeable membrane materials are also hydroxypropyl methylcellulose and polymeric epoxides, copolymers of alkylene oxides and alkyl glycidyl ethers, polyglycols or polylactic acid derivatives and further derivatives thereof. It is also possible to use mixtures, e.g. of water-insoluble acrylates (e.g. the copolymer of ethyl acrylate and methyl methacrylate).

Carbamazepine is used in freely particulate form for the therapeutic system of the present invention. The expression "freely particulate form" will be understood as comprising micronised amorphous anhydrous and micronised crystalline hydrate forms. Micronised crystalline anhydrous forms are preferred. The particle size must be chosen such that unhindered release of the active substance through the orifice of the wall (a) is ensured, which orifice has a preferred diameter of c. 0.4–min. Further, this particle size permits enhanced resorption of dispersed particles of the sparingly soluble drug. In a preferred embodiment of the dosage form of this invention, anhydrous crystals of carbamazepine having an average particle size smaller than 100 μm, preferably smaller than 20 μm, are used.

Protective colloids which inhibit the crystal growth of carbamazepine in the presence of water delay the formation of crystal forms that prove troublesome on a production scale and are unsuitable for the preparation of oral therapeutic systems, e.g. large hydrate crystals of fine grain particles. Surprisingly, such protective colloids inhibit in particular the formation of large needle-shaped crystals (dihydrate crystals) of anhydrous modifications or amorphous particles. As mentioned previously, the formation of large needle-shaped crystals is deleterious to the continuous release performance of the therapeutic system, as the passageway for the delivery of the active substance becomes blocked and consequently release of the drug is hindered.

Particularly suitable protective colloids are dispersible cellulose ethers, e.g. alkylated cellulose such as methyl or ethyl cellulose, hydroxypropyl cellulose, hydroxypropyl alkylcellulose, e.g. hydroxypropyl methyl- or ethylcellulose, carboxymethyl cellulose in salt form, e.g. sodium carboxymethyl cellulose, or carboxymethyl alkylcellulose in salt form, e.g. sodium carboxymethyl methylcellulose or sodium carboxymethyl ethylcellulose.

The most suitable protective colloids are methylated cellulose esters, e.g. methyl cellulose having a methoxy content of c. 27.0 to 32.0% and a degree of substitution of c. 1.75 to 2.1, or hydroxypropyl methylcellulose having a methoxy content of c. 16.0 to 30% and a hydroxypropoxy content of 4.0 to 32.0%. The oral therapeutic system of this invention contains protective colloids such as hydroxypropyl methylcellulose in a preferred mount by weight of c. 5–20%, based on the amount of active substance.

The addition of such protective colloids inhibits or slows down the growth observable in aqueous phase of anhydrous carbamazepine microcrystals having a size of up to c. 100 μm, preferably up to c. 20 μm, or hydrates thereof of similar size, to needle-shaped hydrates having a size of up to c. 500 μm.

The therapeutic system of this invention is therefore able to release carbamazepine microcrystals having a size of up to c. 20 μm into the gastrointestinal tract, so that this drug, in particularly finely dispersed form, can be dissolved and resorbed.

The swellable hydrophilic polymer present in the core (b) is an excipient that interacts with water or the aqueous fluid present in the gastrointestinal tract, swells, and expands to a state of equilibrium. The swellable hydrophilic polymer has the ability to absorb large amounts of water and to induce the pressure necessary for the therapeutic system to function. As the semi-permeable wall (a) is rigid, or at least of only limited elasticity, the pressure induced by expansion is compensated for by release of the material present in the core through the passageway (c) provided in the semi-permeable wall.

Examples of suitable swellable hydrophilic polymers are polymers which may be uncrosslinked or in which, if crosslinked, the crosslinks are formed by covalent or ionic bonds. The polymer retains the ability to swell in the presence of fluids without dissolving completely in the fuid when crosslinked. The polymers can be of plant, animal, mineral or synthetic origin.

Polymers which are paraticularly suitable for use in the practice of this invention are water-soluble aliphatic or cyclic poly-N-vinylamides, e.g. poly-N-vinylmethylacetamide, poly-N-vinylethylacetamide, poly-N-vinylmethylpropionamide, poly-N-vinylethylpropionamide, poly-N-vinylmethylisobutyramide, poly-N-vinyl-2-pyrrolidone, poly-N-vinyl-2-piperidone, poly-N-vinyl-ε-caprolactam, poly-N-vinyl-5-methyl-2-pyrrolidone or poly-N-vinyl-3-methyl-2-pyrrolidone, preferably poly-N-vinylpyrrolidone having an average molecular weight of c. 10,000 to 360,000, swellable polyvinyl acetate or polyvinyl alcohol having a different acetate or residual acetate content, e.g. polyvinyl acetate having a molecular weight of c. 5000 to 400,000, or polyvinyl alcohol having a degree of hydrolysis of c. 85–98% and a degree of polymerisation of c. 500 to 2500, alkylene oxide homopolymers, e.g. polypropylene oxide, preferably ethylene oxide homopolymers having a degree of polymerisation of c. 2000 to 100,000 and known e.g. under the registered trademark Polyox® (Union Carbide), as well as the known protective colloids of the swellable cellulose ether type, e.g. methyl cellulose, ethyl cellulose or hydroxypropyl cellulose or hydroxypropyl methylcellulose, preferably having a molecular weight higher than 10,000, or mixtures of said swellable hydrophilic polymers.

Further suitable swellable hydrophilic polymers are homopolymers such as polyhydroxy alkylmethacrylate having a molecular weight of 5000 to 5000,000, anionic or cationic hydrogels, mixtures of agar and carboxymethyl cellulose, swellable agents consisting of methyl cellulose in admixture with lightly crosslinked agar, water-swellable polymers which can be obtained by dispersing the freely particulate copolymer of maleic anhydride and styrene, as well as polyalkylenes, e.g. polyethylene, polypropylene or polyisobutylene.

In a preferred embodiment of the invention, the swellable hydrophilic polymer is a copolymer of vinylpyrrolidone and vinyl acetate, preferably having a molecular weight of 60,000±15,000. The ratio of vinylpyrrolidone and vinyl acetate in the copolymer is c. 60:40 (% by weight). The copolymer of vinylpyrrolidone and vinyl acetate has the following properties:

Purity: 95% (remainder: water), insoluble in ether and aliphatic hydrocarbons, very readily soluble in water, ethyl and isopropyl alcohol, methylene, chloride, glycerol and 1,2-propylene glycol, pH of a 10% aqueous solution 3–5, viscosity (in 10% aqueous solution): 5 mPa·s (q.v. H. P. Fiedler, Lexikon der Hilfsstoffe, Editio Cantor 1982).

Copolymers of vinylpyrrolidone and vinyl acetate are known and can be obtained in a manner known per se in any ratio of the monomers. The preferred 60:40 copolymer is e.g. available under the registered trademark Kollidon® VA 64 (BASF).

In a particularly preferred embodiment of the invention, a mixture of the copolymer of vinylpyrrolidone and vinyl acetate with an ethylene oxide homopolymer is used as swellable hydrophilic polymer. This mixture has the surprising advantage that the pressure induced by the swelling of the polymer does not lead to rupture of the system and the rate of swelling is uniform, so that approximately constant mounts of active substance are released by the system.

The ethylene oxide homopolymer used in the mixture is Polyox® having a molecular weight higher than $1.0\times10^6$.

In this preferred embodiment of the invention a 1:1 mixture (% by weight) of the copolymer of vinyipyrrolidone and vinyl acetate (commercial form: Kollidon® VA 64) with the ethylene oxide homopolymer (commercial form: Polyox®, mol. wt. $5\times10^6$) is most conveniently used.

The core of the therapeutic system can contain c. 5–60% by weight of swellable hydrophilic polymer, based on the total weight of the therapeutic system.

The optional water-soluble compounds for inducing osmosis which may also be present in the core in addition to the swellable hydrophilic polymer induce an osmotic pressure after water penetrates the semi-permeable membrane and increase the pressure exerted by the hydrophilic polymer.

Water-soluble compounds suitable for inducing osmosis are, in principle, all pharmacologically acceptable water-soluble compounds. e.g. the water-soluble excipients referred to in pharmacopeias or in "Hager" as well as in Remington's Pharmaceutical Sciences. Especially suitable are pharmaceutically acceptable water-soluble salts of inorganic or organic acids or nonionic organic compounds of particularly high water solubility, e.g. carbohydrates such as sugar, or amino acids.

Examples of such water-soluble compounds for inducing osmosis are: inorganic salts such as magnesium chloride or magnesium sulfate, lithium, sodium or potassium chloride, lithium, sodium or potassium hydrogen or dihydrogen phosphate, salts of organic acids such as sodium or potassium acetate, magnesium succinate, sodium benzoate, sodium titrate or sodium ascorbate; carbohydrates such as sorbitol or mannitol (hexite), arabinose, ribose or xylose (pentosene), glucose, fructose, galactose or mannose (hexosene), sucrose, matrose or lactose (disaccharides) or raffinose (trisaccharides); water-soluble amino acids such as glycine, leucine, alanine or methionine, urea and the like, and mixtures thereof. These water-soluble excipients may be present in the core in amounts by weight of c. 0.01 to 35%, based on the total weight of the therapeutic system.

In addition to containing the water-soluble compounds for inducing osmosis and the swellable hydrophilic polymer, the core (b) can contain further pharmaceutically acceptable excipients.

Preferred additional excipients are surface-active compounds. i.e. surfactants, e.g. anionic surfactants of the alkylsulfate type such as sodium, potassium or magnesium n-dodecylsulfate, n-tetradecylsulfate, n-hexadecylsulfate or n-octadecylsulfate, of the alkyl ether sulfate type, e.g. sodium, potassium or magnesium n-dodecyloxyethyl sulfate, n-tetradecyloxyethyl sulfate, n-hexadecyloxyethyl sulfate or n-octadecyloxyethyl sulfate; or of the alkylsulfonate, type e.g. sodium, potassium or magnesium n-dodecanesulfonate, e.g. sodium, potassium or magnesium n-tetradecanesulfonate, n-hexadecanesulfonate or n-octadecanesulfonate.

Further suitable surfactants are nonionic surfactants of the fatty acid polyhydroxy alcohol ester type such as sorbitan monolaurate, sorbitan monooleate, sorbitan monostearate or sorbitan monopalmitate, sorbitan tristearate or triolate, polyethylene glycol fatty acid ester such as polyoxyethyl stearate, polyethylene glycol 400 stearate, polyethylene glycol 2000 stearate, preferably ethylene oxide/propylene oxide block polymers of the Pluronics® (BWC) or Synperonic® (ICI) type.

Further excipients are those customarily used in tabletting for the preparation of granulates, e.g. binders, lubricants, glidants, dispersants, fillers and the like. Thus is it possible to use conventional auxiliaries such as lactose, sacchrose, sorbitol, mannitol, starch, e.g. potato starch, corn starch or amylopectin, or cellulose, especially microcrystalline cellulose, or magnesium stearate, in addition to the cited excipients.

The expression "passageway through the walls (c) for delivering the components present in the core to the environmental aqueous body fluid" encompasses means and methods suitable for releasing the drug formulation from the core of the therapeutic system. The expression comprises passages, orifices, bores, apertures and the like through the wall (a) acting as semi-permeable membrane which establish a connection between the surface of the wall and the core. In one embodiment of the invention, two or more passageways can be provided, which may be located anywhere in the system. The passageway can also be made by mechanical rupture of the layers while the system is in use. The passageway has a minimum diameter which is dependent on the size of the drug crystals. The diameter of the passageway must be greater than the average length of the drug crystals. The maximum diameter is also approximately fixed. It may only be so large that the entry of the aqueous body fluid into the therapeutic system by convection is avoided. An exact description of the passageway and of the maximum and minimum dimensions will be found in U.S. Pat. Nos. 3,485,770 and 3,916,899 and in the drawings pertaining thereto.

The therapeutic system may differ in shape and be e.g. round, oval, tubular and the like, and may also differ in size, depending on the mount of fill material. Furthermore, the therapeutic system can be transparent, colourless or coloured, so as to impart an individual appearance or immediate identification to the product.

The oral therapeutic system of this invention has valuable pharmacological properties and can be used in particular for the treatment of severe painful conditions and convulsions of different provenance, e.g. for the treatment of epilepsy. The use of the above described therapeutic system for the treatment of these diseases, especially epilepsy, constitutes a further object of the invention.

The present invention relates preferably to an oral therapeutic system comprising (a) a wall made of acylated cellulose, e.g. cellulose acetate, which is permeable to water but impermeable to the components of the drug-containing core and to the ions present in body fluids, e.g. gastric or intestinal juices, (b) a core containing freely particulate carbamazepine as drug, hydroxymethyl cellulose as protective colloid, a 1:1 mixture (% by weight) of a copolymer of vinylpyrrolidone and vinyl acetate and a homopolymer of ethylene oxide as swellable hydrophilic polymer, sodium or potassium chloride, glucose or mannitol as agent for inducing osmosis, as well as further pharmaceutically acceptable excipients, and (c) a passageway through the wall (a) for delivering the components present in the core to the environmental aqueous body fluid.

Most preferably the invention relates to an oral therapeutic system comprising (a) a wall made of acylated cellulose, e.g. cellulose acetate, which is permeable to water but impermeable to the components of the drug-containing core and to the ions present in body fluids, e.g. gastric or intestinal juices, (b) a core containing carbamazepine as drug, hydroxypropyl methylcellulose as protective colloid, a 1:1 mixture (% by weight) of a copolymer of vinylpyrrolidone and vinyl acetate having a molecular weight of 60,000±15,000 and having a monomer ratio of c. 60:40 (% by weight) and a homopolymer of ethylene oxide having a degree of polymerisation of 2000 to 100,000 as swellable hydrophilic polymer, sodium or potassium chloride, glucose or mannitol as agent for inducing osmosis, and (c) a passageway through the wall (a) for delivering the components present in the core to the environmental aqueous body fluid.

First and foremost, the invention relates to a therapeutic system for the peroral administration of carbamazepine having the formulation as indicated in the Examples.

The therapeutic system of this invention is prepared by methods which are known per se, e.g. by mixing the components of the core together and compressing them, coating the core with a semi-permeable wall and, if appropriate, providing a passageway through said semi-permeable wall, e.g. an orifice. In a preferred embodiment of the process of this invention, an anhydrous crystal form of carbamazepine is comminuted to an average particle size of 5 μm. These particles, preferably microcrystals, are mixed with the components forming the core of the dosage form and the mixture is granulated, e.g. by mixing the hydroxypropyl methylcellulose or methyl cellulose used as protective colloid, sodium chloride and sodium lauryl sulfate (surfactant) as well as Polyox® with the drug, adding to this mixture a solution of polyvinylpyrrolidone and vinyl acetate in an organic solvent, stripping off the solvent, and granulating and drying the residue. The granulate is then compressed and punched to mouldings, e.g. tablet cores, with or without the addition of a lubricant such as magnesium stearate, which cores are of conventional form and size of e.g. c. 5–12 mm in diameter (round forms) and c. 4–8 mm (in width) and c. 10–22 mm (oblong forms).

To prepare the granulate it is possible to use all solvents in which the swellable hydrophilic polymer and the other auxiliaries are soluble, preferably water or a lower alkanol such as methanol, ethanol or isopropanol.

The core containing the drug formulation can be coated with the semi-permeable wall by coating, moulding, spraying, or immersing the capsule in a solution of the material forming the semi-permeable wall. Another method which may be suitably used for applying the semi-permeable membrane is the air suspension procedure. This method comprises suspending and tumbling the capsule cores in a stream of air and in a composition that forms the wall until the cores sat surrounded and coated by the wall. The air suspension procedure is described in U.S. Pat. No. 2,799,241 and in J. Am. Pharm. Assoc., Vol. 48, pp. 451–459, and in Vol. 49, pp. 82–84, 1980. Other preferred standard procedures are e.g. the pan coating method described in Remington's Pharmaceutical Sciences, 14th edition, pp. 1686–87.

The passageway in the send-permeable wall can subsequently be produced by mechanical or laser drilling. The following Examples illustrate the invention in more detail without limiting the scope thereof.

EXAMPLE 1

Therapeutic system for TEGRETOL ® 200 mg) Core

| | |
|---|---|
| anhydrous carbamazepine (Tegretol ®) | 200 mg |
| microcrystalline cellulose (Avicel ®), FMC Corporation, Philadelphia) | 20 mg |
| hydroxypropyl methylcellulose (Pharmacoat ® 603, Shin-Etsu Chem. Co., Tokyo) | 12.5 mg |
| copolymer of vinylpyrrolidone and vinyl acetate 60:40 (Kollidon ® VA 64, BASF Ludwigshafen) | 80 mg |
| polyethylene glycol (mol. wt. $5 \times 10^6$, Polyox ®, coagulant, Union Carbide) | 80 mg |
| sodium chloride (puriss.) | 80 mg |
| sodium lauryl sulfate (puriss.) | 6 mg |
| magnesium stearate (puriss.) | 11.5 mg |
| | = 490 mg |
| Semi-permeable wall | |
| cellulose acetate (32.0) (puriss.) | 16 mg |
| cellulose acetate (39.9) (puriss.) | 20 mg |
| polyethylene glycol 4000 | 4 mg |
| | = 40 mg |
| Total weight | 530 mg |

Anhydrous carbamazepine, hydroxypropyl methylcellulose, sodium chloride and sodium lauryl sulfate are mixed in a planetary mixer. This mixture is granulated with one part of the copolymer of vinylpyrrolidone and vinyl acetate, dissolved in a mixture of methanol and isopropanol. The mixture is passed through a sieve and the resultant granulate is vacuum dried.

The dry granulate is mixed with the remainder of the copolymer of vinylpyrrolidone and vinyl acetate, Avicel ® and magnesium stearate. The homogeneous mixture is subsequently compressed and punched to tablet cores (punch dimensions: 10 mm, R15).

The cores are coated in a fluidised bed coater (Aeromatic Strea ® 1) with an organic lacquer containing the components of the semi-permeable wall. The coated tablets are dried in an oven at 40° C. for 48 hours. An orifice of 750 μm diameter is drilled with a mechanical drill or with a laser.

EXAMPLE 2

Therapeutic system for TEGRETOL ® (200 mg) Core

| | |
|---|---|
| anhydrous carbamazepine (Tegretol ®) | 200 mg |
| microcrystalline cellulose (Avicel ®, FMC Corporation, Philadelphia) | 20 mg |
| hydroxypropyl methylcellulose (Pharmacoat ® 603, Shin-Etsu Chem. Co., Tokyo) | 13 mg |
| copolymer of vinylpyrrolidone and vinyl acetate 60:40 (Kollidon ® VA 64, BASF Ludwigshafen) | 80 mg |
| hydroxyethyl cellulose (Tylose ® H 4000 PHA) | 80 mg |
| glucose (puriss.) | 90 mg |
| sodium lauryl sulfate (puriss.) | 7 mg |
| magnesium stearate (puriss.) | 10 mg |
| | = 500 mg |

Semi-Permeable Wall

| | |
|---|---|
| cellulose acetate (32.0) (puriss.) | 16 mg |
| cellulose acetate (39.9) (puriss.) | 20 mg |
| polyethylene glycol 4000 | 4 mg |
| | = 40 mg |

-continued

| | |
|---|---|
| Total weight | 540 mg |

Preparation is as described in Example 1. Hydroxyethyl cellulose is used as swellable hydrophilic polymer instead of polythylene glycol (mol. wt. $5 \times 10^6$). Glucose is used instead of sodium chloride as agent for inducing osmosis. The granulate is prepared by mixing the components with an ethanolic solution which contains one part of Kollidon ® VA 64.

EXAMPLE 3

Therapeutic system for TEGRETOL ® 200 mg) Core

| | |
|---|---|
| anhydrous carbamazepine (Tegretol ®) | 200 mg |
| microcrystalline cellulose (Avicel ®, FMC Corporation, Philadelphia) | 20 mg |
| hydroxypropyl methylcellulose (Pharmacoat ® 603, Shin-Etsu Chem. Co., Tokyo) | 12.5 mg |
| copolymer of vinylpyrrolidone and vinyl acetate 60:40 (Kollidon ® VA 64, BASF Ludwigshafen | 81.3 mg |
| polyethylene glycol (mol. wt. $5 \times 10^6$, Polyox ®, coagulant, Union Carbide) | 80 mg |
| sodium lauryl sulfate (puriss.) | 6 mg |
| magnesium stearate (puriss.) | 10.2 mg |
| | = 410 mg |

Semi-Permeable Wall

| | |
|---|---|
| cellulose acetate (32.0) (puriss.) | 16 mg |
| cellulose acetate (39.9) (puriss.) | 20 mg |
| polyethylene glycol 4000 | 4 mg |
| | = 40 mg |
| Total weight | 450 mg |

Preparation of the oral therapeutic system is as described in Example 1. The use of an osmotic agent is dispensed with.

EXAMPLE 4

Therapeutic system for TEGRETOL ® 200 mg) Core

| | |
|---|---|
| anhydrous carbamazepine (Tegretol ®) | 200 mg |
| hydroxypropyl methylcellulose (Pharmacoat ® 603, Shin-Etsu Chem. Co., Tokyo) | 25 mg |
| hydroxyethyl cellulose (Natrosol ® 250L, Hercules) | 25 mg |
| hydroxyethyl cellulose (Natrosol ® 250H) | 25 mg |
| mannitol (puriss.), | 215 mg |
| sodium lauryl sulfate (puriss.) | 5 mg |
| magnesium stearate (puriss.) | 5 mg |

| | |
|---|---|
| cellulose acetate (32.0) (puriss.) | 18.9 mg |
| cellulose acetate (39.8) (puriss.) | 2.8 mg |
| hydroxypropyl methylcellulose 15 CPS | 2.1 mg |
| polyethylene glycol 8000 | 2.1 mg |
| | = 26 mg |
| Total weight | 526 mg |

Preparation is as described in Example 1. Hydroxyethyl cellulose is used as swellable hydrophilic polymer instead of polyethylene glycol and Kollidon ®. Mannitol is used instead of sodium chloride as agent for inducing osmosis. The granulate is prepared by mixing the components with an ethanolic solution which contains 1 part of the hydroxyethyl cellulose employed.

What is claimed is:

1. An oral therapeutic system for administering carbamazepine comprising (a) a wall made of acylated cellulose which is permeable to water but impermeable to the components of the drug containing core and to the ions present in gastric or intestinal juices;

(b) a core containing finely particulate carbamazepine as a drug, hydroxypropylmethyl cellulose as protective colloid, a swellable hydrophilic polymer selected from the group consisting of poly-N-vinyl-2-pyrrolidone, polyvinyl alcohol, alkylene oxide homopolymers, methyl cellulose, ethyl cellulose, hydroxypropyl cellulose, the copolymer of vinylpyrrolidone and vinyl acetate, the mixture of the copolymer of vinylpyrrolidone and vinyl acetate and the homopolymer of ethylene oxide and, a water soluble compound for inducing osmosis; and (c) a passageway through the wall (a) for delivering the components present in the core to the environmental gastric or intestinal juices.

2. An oral therapeutic system according to claim 1, comprising (a) a wall made of acylated cellulose which is permeable to water but impermeable to the components of the drug-containing core and to the ions present gastric or intestinal juices, (b) a core containing finely particulate carbamazepine as drug, hydroxymethyl cellulose as protective colloid, a 1:1 mixture % by weight of a copolymer of vinylpyrrolidone and vinyl acetate and a homopolymer of ethylene oxide as swellable hydrophilic polymer, and and (c) passageway through the wall (a) for delivering the components present in the core to the environmental aqueous body fluid.

3. An oral therapeutic system according to claim 1, comprising (a) a wall made of cellulose acetate which is permeable to water but impermeable to the components of the drug-containing core and to the ions present in gastric or intestinal juices, (b) a core containing carbamazepine as drug, hydroxypropyl methylcellulose as protective colloid, a 1:1 mixture % by weight of a copolymer of vinylpyrrolidone and vinyl acetate having a molecular weight of 60.000±15,000 and having a monomer ratio of 60:40% by weight and a homopolymer of ethylene oxide having a degree of polymerisation of 2000 to 100,000 as swellable hydrophilic polymer, and (c) a passageway through the wall (a) for delivering the components present in the core to the environmental gastric or intestinal juices.

4. An oral therapeutic system according to claim 1, which contains anhydrous microcrystals of carbamazepine.

5. An oral therapeutic system according to claim 1, which contains anhydrous microcrystals of carbamazepine having a size of up to 20 μm, and hydroxypropyl methylcellulose as protective colloid.

6. The therapeutic system of claim 2 further comprising a compound for inducing osmosis selected from sodium chloride, potassium chloride, glucose, and mannitol.

7. The therapeutic system of claim 3 further comprising a compound for inducing osmosis selected from sodium chloride, potassium chloride, glucose and mannitol.

*8. An oral therapeutic system for administrating carbamazepine comprising*

*(a) a wall made of acylated cellulose which is permeable to water but impermeable to the components of the drug containing core and to the ions present in gastric or intestinal juices;*

*(b) a core containing finely particulate carbamazepine as a drug, hydroxypropylmethyl cellulose as protective colloid, a swellable hydrophilic polymer selected from the group consisting of poly-N-vinyl-2-pyrrolidone, polyvinyl alcohol, alkylene oxide homopolymers, methyl cellulose, ethyl cellulose, hydroxypropyl cellulose, hydroxyethyl cellulose, the copolymer of vinyl pyrrolidone and vinyl acetate, the mixture of the copolymer of vinylpyrrolidone and vinyl acetate and the homopolymer of ethylene oxide and, a water soluble compound for inducing osmosis; and*

*(c) a passageway through the wall (a) for delivering the components present in the core to the environmental gastric or intestinal juices.*

*9. The oral therapeutic system of claim 8 wherein 2 swellable hydrophilic polymers are present.*

*10. The oral therapeutic system of claim 8 wherein said carbamazepine is present as anhydrous microcrystals.*

*11. The oral therapeutic system of claim 10 wherein carbamazepine microcrystals have a size of up to 20um, and said protective colloid is hydroxypropyl methylcellulose.*

*12. The oral therapeutic system of claim 8 further comprising a compound for inducing osmosis selected from sodium chloride, potassium chloride, and carbohydrates.*

*13. The oral therapeutic system of claim 11 further comprising a compound for inducing osmosis selected from sodium chloride, potassium chloride, and carbohydrates.*

*14. The oral therapeutic system of claim 8 wherein said core comprises anhydrous carbamazepine, hydroxypropyl methylcellulose, hydroxyethylcellulose, and mannitol.*

*15. The oral therapeutic system of claim 8 wherein said wall comprises cellulose acetate, hydroxypropyl methylcellulose, and polyethylene glycol 8000.*

* * * * *